United States Patent [19]

Sedun

[11] Patent Number: 5,395,851
[45] Date of Patent: * Mar. 7, 1995

[54] TREE WOUND COATING COMPOSITION

[75] Inventor: Frederick S. Sedun, Saanichton, B.C., Canada

[73] Assignee: W. Neudorff GmbH KG, Germany

[*] Notice: The portion of the term of this patent subsequent to Sep. 21, 2010 has been disclaimed.

[21] Appl. No.: 93,460

[22] Filed: Jul. 16, 1993

Related U.S. Application Data

[63] Continuation of Ser. No. 818,843, Jan. 10, 1992, abandoned.

[51] Int. Cl.⁶ ............... A01N 55/02; A01N 57/12; A01N 37/02; A01N 37/06
[52] U.S. Cl. ..................... 514/494; 514/78; 514/492; 514/499; 514/502; 514/529; 514/549; 514/552; 514/557; 514/558; 514/560; 514/739; 514/770; 514/774; 514/777; 514/779; 514/780; 514/781; 514/782; 514/784; 514/773; 514/937; 514/943; 514/949; 514/785; 424/520; 424/522; 424/526; 424/537
[58] Field of Search ............ 514/494, 499, 502, 492, 514/558, 560, 78, 529, 549, 552, 557, 739, 770, 773, 774, 779, 780, 781, 782, 784, 785, 937, 943, 949, ; 424/520, 522, 526, 537

[56] References Cited

U.S. PATENT DOCUMENTS

| | | | |
|---|---|---|---|
| 2,466,663 | 4/1949 | Russ et al. | 514/558 |
| 3,931,413 | 1/1976 | Frick et al. | 514/557 |
| 4,001,400 | 1/1977 | Hager | 514/558 |
| 4,177,288 | 12/1979 | Gohlke | 424/705 |
| 4,179,522 | 12/1979 | Huitson | 514/558 |
| 4,242,357 | 12/1980 | Fuchs et al. | 514/464 |
| 4,532,161 | 7/1985 | Collins | 514/494 |
| 4,585,795 | 4/1986 | Linderborg | 514/558 |
| 5,093,124 | 3/1992 | Kulenkampff | 424/406 |
| 5,143,932 | 9/1992 | Jautelat et al. | 514/383 |
| 5,246,716 | 9/1993 | Sedun et al. | 424/713 |

FOREIGN PATENT DOCUMENTS

| | | |
|---|---|---|
| 59-2224 | 1/1984 | Japan . |
| 59-221389 | 12/1984 | Japan . |
| 8903178 | 4/1989 | WIPO . |

OTHER PUBLICATIONS

Farm Chemicals Handbook '87, Meister Publishing Co., Ohio, 1987, p. C273.
Chemical Abstracts 92:82944X (1980).
Chemical Abstracts: 85:15347W (1976).
Chemical Abstracts 102: 98193n (1985).

*Primary Examiner*—Allen J. Robinson
*Assistant Examiner*—John D. Pak
*Attorney, Agent, or Firm*—Lahive & Cockfield

[57] ABSTRACT

A coating composition for application to tree wounds, such as pruning wounds of living trees is provided. The composition is non-phytotoxic and provides extended protection against fungal pathogens. The coating composition comprises a liquid carrier together with a fatty acid metal salt active ingredient. Exemplary fatty acid metal salts include those prepared from alpha monocarboxylic acids having from 4 to 18 carbon atoms and a compound containing a metal selected from the group consisting of calcium, copper, iron, magnesium, and zinc. Various additives can be included within the composition, including gum-like substances and binders suitable to facilitate the adhesion of the active ingredient to the tree surface, as well as defoaming agents and other formulation enhancing agents.

3 Claims, No Drawings

TREE WOUND COATING COMPOSITION

"This application is a continuation of application Ser. No. 818,843, filed on Jan. 10, 1992", now abandoned.

BACKGROUND OF THE INVENTION

The present invention relates to coating compositions for application to tree wounds, such as those which result from tree pruning. More importantly, the invention relates to tree coating compositions having anti-fungal properties.

During a pruning procedure, branches or limbs are cut from a living tree or bush. The resulting exposed tree wound renders the tree susceptible to infection by fungal pathogens as the wound provides a suitable environment for the growth of such fungi.

Currently, various compositions are available for application to pruning wounds and other tree wounds, primarily to provide a coating over the exposed wood tissue. Such compositions, collectively referred to herein as "pruning paints", usually are tars or putty-like materials which simply cover the wound. However, the act of sealing the wound can be a drawback of using such materials because by the time the pruning paint is applied, fungi may have already infected the wound. Also the sealed, moist environment on the wood surface caused by some pruning paints can be ideal for the growth of fungi. Known pruning paints are not believed to have any ability to kill or control the growth of fungi.

While a variety of fungicidal agents are known, they generally are not suitable for use in a pruning paint composition because they exhibit phytotoxic as well as fungicidal properties. The application of such materials to a tree wound could severely damage the cambium of a tree.

Accordingly, there is a need for an effective pruning paint composition which safely can be applied to tree wounds, such as pruning wounds, to facilitate the healing of the wound while preventing fungal infection.

It is thus an object of the invention to provide a non-phytotoxic coating composition able to be applied to tree wounds to promote healing of the wound. It is also an object to provide such a composition which has sufficient anti-fungal properties to prevent the growth and colonization of fungal pathogens within the tree. Another object is to provide an environmentally compatible pruning paint composition which is able to protect against fungal infection for an extended duration. A further object of the invention is to provide a method of coating pruning wounds and other tree wounds to promote healing and to prevent fungal infection. Other objects will be apparent upon reading the disclosure which follows.

SUMMARY OF THE INVENTION

The present invention relates to an environmentally compatible pruning paint composition which is non-phytotoxic and which exhibits anti-fungal properties. The composition is suitable for application to tree wounds, such as pruning wounds, to promote healing and drying of the wound while protecting the tree from fungal pathogens.

The composition comprises a carrier or binder and a non-phytotoxic, anti-fungal active ingredient. The active ingredient comprises a fatty acid metal salt formed from one or more alpha monocarboxylic fatty acids having from 4 to 18 carbon atoms and a metal compound containing a metal selected from the group consisting of calcium, copper, iron, magnesium and zinc. The concentration of the active ingredient in compositions applied to tree wounds generally is in the range of 1 to 20 percent by weight of the total composition, and in some instances it can be as high as 40 percent by weight.

The composition may also include additives such as one or more gum-like materials to promote adhesion of the active ingredient to the tree wound. Various formulation enhancing additives, such as defoaming agents and anti-freezing agents, may also be included.

A particular advantage of the composition is that the anti-fungal properties are able to persist for several weeks. Moreover, the composition may take the form of a sprayable liquid or a spreadable paste.

DETAILED DESCRIPTION OF THE INVENTION

The coating composition of this invention is suitable for application to wounds on living trees, including pruning wounds, stump wounds and root wounds. The composition serves to promote healing and drying of the wound while preventing fungal pathogens from infecting the tree through the wound and causing damage to the tree.

The composition preferably comprises a liquid carrier (or a solid binder) within which a fatty acid metal salt active ingredient is disposed. The fatty acid metal salt active ingredient is formed from one or more alpha monocarboxylic fatty acids having from 4 to 18 carbon atoms and a compound containing a metal selected from the group consisting of calcium, copper, iron, magnesium, and zinc. In one embodiment, the composition also includes a gum or gum-like material which serves to enhance the ability of the active ingredient to adhere to the tree wound. Various formulation enhancing additives, such as defoaming and anti-freezing agents, may be added to the composition as well.

The composition may take the form of a liquid or paste. Liquid forms of the present pruning paint composition may be applied to the wound of a tree by spraying or painting. Paste-like compositions may be spread over the wound, or, in some instances, may be sprayed. The composition typically dries within 2 hours and retains its fungicidal effect for as long as 2 months.

As noted, the fatty acid metal salt active ingredient may comprise a metal salt of one or a mixture of alpha monocarboxylic fatty acids having from 4 to 18 carbon atoms. More preferably, the fatty acid metal salts have from 6 to 12 carbon atoms, and most preferably from 8 to 10 carbon atoms. Metal ions from which the salts can be formed include $Mg^{+2}$ $Ca^{+2}$ $Fe^{+2}$ $Fe^{+3}$ $Cu^{+1}$ $Cu^{+2}$ and $Zn^{+2}$. The ferric, magnesium and calcium salts of the fatty acids are among the most preferred due to their combination of fungicidal properties and virtual absence of phytotoxicity. Particularly preferred metal salt active ingredients are calcium octanoate, ferric octanoate, magnesium octanoate, zinc octanoate, calcium nonanoate, ferric nonanoate, magnesium nonanoate and zinc nonanoate. Mixtures of these fatty acid metal salts may also form the active ingredient of the pruning paint.

An additional benefit of using ferric and ferrous fatty acid salts is that the iron reacts with the wood, turning the wood grey. The wood remains grey even after all of the pruning paint is removed. It is believed that this reaction causes chemical changes in the wood, making it less suitable as a substrate for fungi.

One skilled in the art will appreciate that the concentration of fatty acid metal salt active ingredient in the composition applied to a tree wound will vary depending upon the chain length of the compounds as well as the metal cation involved. In one embodiment, up to about 40 percent by weight of the active ingredient may be present in the composition. Typically, however, a concentration of 1 to 20 percent by weight achieves suitable fungicidal activity. Most preferably, the concentration of the fatty acid metal salt active ingredient in the applied coating composition is the range of 3 to 10 percent by weight.

Although the fatty acid metal salt compound is suitably effective as a sole active ingredient, it is possible to include additional active ingredients which do not exhibit phytotoxicity. Examples of additional suitable active ingredients include lanolin and lecithin-based compositions such as BioBlatt, a composition commercially available from W. Neudorff GmbH KG of Emmerthal, Germany.

As noted, gums and gum-like materials preferably are included within the composition to enhance the ability of the active ingredient to adhere to the surface of the tree wound. Such additives may include gums such as guar gum, xanthan gum, cellulose-based materials, Elemi tree gum, and acacia gum. Additional gum-like materials and binders which may be used include polyacrylamide, polyacrylic acid, Bentonite clay, china clay, and magnesium aluminum silicate. Gels such as gelatin and agar may be used as well. A single gum or gum-like material may be used, or various mixtures of these materials may be used. The gums typically are used in the composition in the range of about 0.1 to 2 percent by weight.

An example of a modified cellulose material is Methocel K4M, available from Dow Chemical Company. An example of a useful guar gum is Uniguar 150, available from Rhone Poulenc, Inc. Useful Elemi tree gums include Gum Elemi and Manilla Copal A, both available from O.G. Innes Corp. A suitable Acacia gum is Gum Arabic, available from A1-Don Chem. Inc. Exemplary xanthan gums include Kelgum (Kelco Co.), Kelzan S (Kelco Co.), and Rhodopol 23 (R. T. Vanderbilt). An exemplary magnesium aluminum silicate is Vangel B (R. T. Vanderbilt). An exemplary Bentonite clay is Bentone SD-1 (NL Chem. Inc.). An exemplary China clay is Ecca clay available from E.C.C. America Inc.

In one embodiment, it is useful to include within the composition anti-freezing agents including propylene glycol, ethylene glycol or glycerine. These additives may be used at concentrations ranging from 2.5 to 10 weight percent.

Other property enhancing additives may be present in the composition as well. These include various dispersants and wetting agents which may be used as necessary. One particularly useful additive is a defoaming agent, which is used in very low concentrations in the range of 0.005 to 0.05 percent by weight. An example of a suitable defoaming agent is a silicone-based emulsion, commercially available as Dow FG-10 from Dow Corning Corp, Midland, Michigan. A suitable wetting agent is Aerosol OT75, available from Cyanamid, typically used at a concentration below 0.1 wt. percent.

Preferably, water is the carrier used in liquid compositions. Other carriers which may be used include oils (e.g., refined petroleum distillates, and vegetable oils), and natural alcohols. Examples of refined petroleum distillates include light mineral oils and napthalates. A specific example is Sunspray 6E Plus available from Sun Refining and Marketing Company. Suitable vegetable oils include cottonseed oil, canola oil, and soybean oil. Exemplary natural alchohols include methanol, ethanol, and isopropanol.

The fatty acid metal salt active ingredient may be obtained commercially, or may be prepared by methods well known to those skilled in the art. By way of example, ferric octanoate can be prepared by combining octanoic acid (7.13 grams) with sodium hydroxide (2.02 grams) to yield a soap. An aqueous solution of ferric chloride (2.67 grams) is then added to the soap, causing a reaction which yields ferric octanoate, sodium chloride and water.

The pH of the composition is typically in the range of about 4 to 10.

The invention is further described by the exemplary formulations identified below.

| Formulation A | |
|---|---|
| Ferric octanoate | 8% |
| Magnesium aluminum silicate | 0.8% |
| Xanthan gum | 0.2% |
| Propylene glycol | 5% |
| Defoaming agent | 0.01% |
| Water | Balance |
| Formulation B | |
| Ferric octanoate | 8% |
| Magnesium aluminum silicate | 0.8% |
| Xanthan gum | 0.2% |
| Propylene glycol | 5% |
| Aerosol OT75 | 0.05% |
| Defoaming Agent | 0.01% |
| Water | Balance |
| Formulation C | |
| Ferric octanoate | 8.0% |
| Gelatin | 1.0% |
| Magnesium aluminum silicate | 0.8% |
| Xanthan gum | 0.2% |
| Propylene glycol | 5.0% |
| Defoaming Agent | 0.01% |
| Water | Balance |
| Formulation D | |
| Ferric octanoate | 8.0% |
| Modified Cellulose | 0.25% |
| Propylene glycol | 5.0% |
| Defoaming Agent | 0.01% |
| Water | Balance |
| Formulation E | |
| Ferric octanoate | 8.0% |
| China Clay | 5.0% |
| Magnesium aluminum silicate | 0.8% |
| Xanthan gum | 0.2% |
| Propylene glycol | 5.0% |
| Defoaming agent | 0.01% |
| Water | Balance |

Formulations A through E provide examples of suitable combinations of additives which may be included within the coating composition of the invention. In each of the above formulations, the ferric octanoate active ingredient may be replaced with other fatty acid metals salts, including ferric nonanoate, calcium octanoate, calcium nonanoate, magnesium octanoate, magnesium nonanoate, or mixtures of fatty acid metal salts. In addition, the concentration of the active ingredient may be varied from between 2 percent and 20 percent by weight, with more or less water being used in the formulation to account for the differential in the amount of active ingredient used. Of the above compositions, Formulation C is currently the most preferred.

In addition to the above formulations, all of which use water as a carrier, oil-based formulations may be used. Formulation F, identified below, provides an example of a formulation in which an oil serves as the carrier.

| Formulation F | |
| --- | --- |
| Ferric octanoate | 1.0% |
| Refined Petroleum distillate | 99.0% |

Formulation F may be varied by substituting other fatty acid metal salts, or mixtures thereof, for the ferric octanoate. In addition, the amount of active ingredient may be varied from between 1 to 10 percent by weight, while making corresponding changes in the amount of carrier used. An example of a refined petroleum distillate suitable for use in the composition is Sunspray 6E Plus, available from Sun Refining and Marketing Company, Philadelphia, PA. Sunspray 6E Plus includes about 98.8% of a refined petroleum distillate and 1.2% of an emulsifier. Other oil carriers which can be used include vegetable oils. Binders and similar additives generally are unnecessary when oil-based carriers are used since oils have the ability to penetrate the wood.

Examples of spreadable compositions are identified below as Formulations G and H, which are paste-like in consistency. As with other exemplary formulations, the identity and amount of the fatty acid metal salt active ingredient may be varied.

| Formulation G | |
| --- | --- |
| Ferric octanoate | 8.0% |
| China Clay | 25.0% |
| Propylene glycol | 5.0% |
| Defoaming agent | 0.01% |
| Water | Balance |
| Formulation H | |
| Ferric octanoate | 8.0% |
| Lanolin | 66.0% |
| Rosin | 13.0% |
| Gum | 13.0% |

Additionally, a powdered concentrate of the type identified below in Formulation I may be used.

| Formulation I | |
| --- | --- |
| Ferric octanoate | 80.0% |
| BioBlatt | 15.0% |
| Aerosol OT75 | 4.9% |
| Aerosil 200 | 0.1% |

Powdered concentrates exemplified by Formulation I may be diluted with water and applied as a sprayable paste or as a spreadable paste. When diluted with an equal amount of water, a spreadable paste is formed having an active ingredient concentration of 40 percent by weight. Alternatively, the powdered concentrate can be diluted with 9 parts of water for each part formulation to yield an 8% ferric octanoate paste which may be sprayed upon a tree wound. As with other exemplary formulations, other fatty acid metal salts may replace and/or supplement the ferric octanoate, and adjustments may be made in the concentrations of the various constituents of the formulation.

An important advantage of the composition of the invention is that the fungicidal properties of the composition are residual, lasting for as long as several weeks. This residual effect is believed to result, in part, from the relatively low solubility in water of the fatty acid metal salts. Solubility of these salts in water is approximately 0.1 to 0.5 g/100mL of water. When using a water carrier, the active ingredient remains dispersed and suspended in the carrier. The carrier (e.g., water) evaporates when applied to a wound surface of a tree. The salt of the fatty acid then remains adhered to the tree surface, sometimes with the aid of gum-like compounds and other binder materials (such as clays). By adhering to the tree surface, the salt of the active ingredient is able to maintain its fungicidal effect for extended periods of time. Similarly, oil carriers enable the active ingredient to adhere to the wound surface while water beads up and runs off the oil coated surface.

The low solubility in water of the fatty acid metal salts also contributes to the low phytotoxicity of the formulation. A very low or non-existent level of phytotoxicity is essential to the composition as it is applied directly to exposed tree tissue. Compositions having phytotoxic potential are not desirable as they could severely damage the tree.

The fatty acid metal salt active ingredient is dispersed in water to form a metal cation and a fatty acid anion. The anion is an agent which is potentially toxic to both fungi and plants. The metal salts of the present invention are much less soluble than are sodium and potassium salts, for example, which are known to be effective phytotoxic agents. The nature of the dynamic equilibrium of the fatty acid metal salt in water is such that the anion and cation concentrations remain constant, provided that there is an excess of the fatty acid metal salts present. The amount of excess salt required and the ion concentration vary depending upon the salt used and the amount of water present. The equilibrium concentration of the anion is such that it is toxic to fungi but not toxic to the tree itself.

As noted, the active ingredient remains adhered to the surface of the tree over a period of time. When it is adhered to the tree in dry form the active ingredient remains a non-dissociated fatty acid metal salt. When rain or other moisture is deposited on the tree, the active ingredient dissociates until the concentration of the anion reaches equilibrium. Upon drying, the anion and cation combine again to form the fatty acid metal salt.

In order for a fungus to colonize wood treated with an oil based pruning paint of the type described herein, the fungus must be able to make the oil water soluble through the action of fungal exudates. It is likely that during this process the fatty acid metal salt which is dissolved in the oil will disperse in the water, forming the fatty acid anion and the corresponding cation.

The fungicidal composition of the present invention is a broad range fungicide which is effective against a variety of pathogenic fungi. Examples of common fungi which the composition is effective against include *Botrytis cinerea, Rhizoctonia Solani* AG4, *Fusarium oxysporum, Pythium* sp., *Aspergillus niger, Penicillium digitatum, Penicillum* sp., *Venturia inaequillus, Colletotrichum lindemuthianum, Erysiphe communis,* and *Heterobasidium annosum.*

The following non-limiting examples serve further to describe the invention.

Unless otherwise noted, the following examples were conducted with exemplary formulation A, using the identified fatty acid metal salt in the stated concentrations.

Example 1

The cambium damage (phytotoxicity) caused by various compositions was assessed by spraying test solutions onto freshly cut branches of *Arbutus menziesii* Pursh. After seven days, the treated branches were removed and the cambium damage was assessed using a scale of 0 (no damage) to 9 (very extensive damage). The cambium damage rating scale is illustrated in Table 1.

TABLE 1

Cambium Damage Rating Scale

| Number Code | Cambium Damage | Acceptability |
|---|---|---|
| 0 | no damage | Acceptable |
| 1 | faint boundary | Acceptable |
| 2 | faint boundary | Acceptable |
| 3 | definite boundary | Acceptable |
| 4 | definite boundary | Acceptable |
| 5 | slight streaking | Marginal acceptance |
| 6 | severe streaking | Not acceptable |
| 7 | severe streaking | Not acceptable |
| 8 | extensive damage | Not acceptable |
| 9 | very extensive damage | Not acceptable |

The ability of a test compound to control the growth of fungi on dead wood was also assessed by dipping wood samples into test solutions. After drying, the wood was innoculated with spores of several fungi, and stored under high relative humidity. Observations were made after 10 days, and again after one month, using a 0 to 9 rating scale for fungal colonization and growth of the wood where 0 represents no growth and 9 represents maximum growth. Fungal growth ratings of less than 4 are acceptable. The Data is illustrated in Tables 2 and 3.

TABLE 2

Cambium Damage and Fungal Growth Data

| Treatment | Cambium Damage | Fungal Growth on Wood |
|---|---|---|
| [1]Ca(C8)$_2$(4%) | 2.0 | 0.0 |
| [2]Fe(C8)$_3$(4%) | 3.0 | 0.0 |
| [3]Zn(C8)$_2$(4%) | 1.6 | 0.3 |
| Sodium borate (4%) | 2.4 | 0.4 |
| Dioctyl sodium sulfosuccinate (2%) | 9.0 | 0.0 |
| Water | 0.0 | 4.4 |
| Untreated | 0.0 | 4.7 |

[1]Calcium octanoate
[2]Ferric octanoate
[3]Zinc octanoate

TABLE 3

Cambium Damage and Fungal Growth Data

| Treatment | Cambium Damage | Fungal Growth on Wood |
|---|---|---|
| Ca(C8)$_2$(8%) | 4.0 | 2.7 |
| [1]Cu(C8)$_2$(8%) | 3.0 | 4.3 |
| [2]Fe(C8)$_2$(8%) | 0.8 | 7.9 |
| [3]Fe(C8)$_3$(8%) | 3.6 | 0.9 |
| [4]Mg(C8)$_2$(8%) | 3.2 | 0.5 |
| [5]Na(C8)(8%) | 6.0 | 1.0 |
| Zn(C8)$_2$(8%) | 1.6 | 4.9 |
| CaCl$_2$ 2.71% | 0.4 | 9.6 |
| FeCl$_2$ 4.65% | 9.0 | 1.3 |
| FeCl$_3$ 2.67% | 8.0 | 3.4 |
| MgSO$_4$ 6.36% | 0.4 | 9.0 |
| ZnCl$_2$ 3.11% | 7.2 | 8.3 |
| Dioctyl sodium sulfosuccinate (2%) | 7.2 | 0.4 |
| [6]Lac Balsam | 1.6 | 6.9 |
| Water | 1.2 | 9.4 |
| Untreated | 2.0 | 9.4 |

[1]Cupric octanoate
[2]Ferrous octanoate
[3]Ferric octanoate
[4]Magnesium octanoate
[5]Sodium octanoate
[6]A commercial pruning paint available from W. Neudorff GmbH KG, Emmerthal, Germany.

EXAMPLE 2

The cambium damage on Arbutus, Douglas fir, Maple, Oak, and Willow caused by various compositions was also assessed. The data is illustrated in Table 4.

TABLE 4

Cambium Damage - Various Tree Species

| Treatment | Arbutus | Douglas fir | Maple | Oak | Willow |
|---|---|---|---|---|---|
| Fe(C8)$_3$(2%) | 2.7 | 1.5 | 0.0 | 4.0 | 2.5 |
| Fe(C8)$_3$(4%) | 4.2 | 4.0 | 0.0 | 5.0 | 4.0 |
| Fe(C8)$_3$(6%) | 4.7 | 3.5 | 0.0 | 4.0 | 4.5 |
| Fe(C8)$_3$(8%) | 5.8 | 2.0 | 3.0 | 7.5 | 4.5 |
| Lac Balsam | 2.5 | 1.0 | 0.0 | 3.5 | 3.5 |
| Dioctyl sodium sulfosuccinate(2%) | 8.2 | 0.0 | 8.5 | 9.5 | 4.5 |
| Dioctyl sodium sulfosuccinate(2%) | 8.3 | 0.0 | 8.0 | 7.5 | 3.0 |
| Fe(Cl)$_3$(8%) | 3.8 | 5.0 | 0.0 | 5.5 | 2.0 |
| Untreated | 1.0 | 0.0 | 0.0 | 0.0 | 2.0 |

EXAMPLE 3

The ability of a test compound (pruning paint) to control the growth of fungi on dead wood was further assessed according to the procedure identified in Example 1.

This data is illustrated in Table 5.

TABLE 5

Fungal Growth Inhibition Data

| Treatment | Fungal Growth Rating (5 weeks) |
|---|---|
| Fe(C8)$_3$(2%) | 7.7 |
| Fe(C8)$_3$(4%) | 4.4 |
| Fe(C8)$_3$(6%) | 2.3 |
| Fe(C8)$_3$(8%) | 0.3 |
| *Fe(C8)$_3$(8%) [B] | 1.0 |
| Lac Balsam | 6.1 |
| Dioctyl sodium sulfosuccinate (2%) | 0.6 |
| Dioctyl sodium sulfosuccinate (1%) | 0.5 |
| FeCl$_3$ 1% | 7.5 |
| Water | 8.8 |
| Untreated | 8.4 |

*Denotes an 8% by wt. concentration of a ferric octanoate active ingredient prepared according to Formulation B.

It is understood that various modifications may be made to the invention described herein without exceeding the scope of the invention.

What is claimed is:

1. A non-phytotoxic fungicidal coating composition for application to wounds on living trees, consisting essentially of:

0.5 to 10% by weight of a fatty acid metal salt ingredient selected from the group consisting of
calcium salt of an alpha monocarboxylic aliphatic $C_{8-12}$ acid, iron salt of an alpha monocarboxylic aliphatic $C_{8-12}$ acid, copper salt of an alpha monocarboxylic aliphatic $C_{8-12}$ acid, zinc salt of an alpha monocarboxylic aliphatic $C_{8-12}$ acid, and mixtures thereof, the fatty acid metal salt ingredient being substantially insoluble in the composition and remaining suspended in the composition;

0.1 to 2% by weight of a thickening agent, selected from the group consisting of guar gum, xanthan gum, cellulose-based gum, Elemi tree gum, acacia gum, Bentonite clay, magnesium aluminum silicate, gelatin, agar, and mixtures thereof; and water;

wherein the coating composition has a pH in the range of about 4 to 10, and is in the form of a non-phytotoxic liquid suspension or a non-phytotoxic spreadable paste.

2. The composition of claim 1 wherein the fungicidal agent is selected from the group consisting of calcium octanoate, ferric octanoate, zinc octanoate, calcium nonanoate, ferric nonanoate, zinc nonanoate, and mixtures thereof.

3. A non-phytotoxic fungicidal coating composition for application to wounds on living trees, consisting essentially of:

0.5 to 10% by weight of a fatty acid metal salt ingredient selected from the group consisting of calcium salt of an alpha monocarboxylic aliphatic $C_{8-12}$ acid, iron salt of an alpha monocarboxylic aliphatic $C_{8-12}$ acid, copper salt of an alpha monocarboxylic aliphatic $C_{8-12}$ acid, zinc salt of an alpha monocarboxylic aliphatic $C_{8-12}$ acid, and mixtures thereof, the fatty acid metal salt ingredient being substantially insoluble in the composition and remaining suspended in the composition;

0.1 to 2% by weight of a thickening agent, selected from the group consisting of guar gum, xanthan gum, cellulose-based gum, Elemi tree gum, acacia gum, Bentonite clay, magnesium aluminum silicate, gelatin, agar, and mixtures thereof;

an additional active ingredient selected from the group consisting of lanolin and lecithin-based compositions; and water;

wherein the coating composition has a pH in the range of about 4 to 10, and is in the form of a non-phytotoxic liquid suspension or a non-phytotoxic spreadable paste.

* * * * *